United States Patent [19]

Stevenson-Michener

[11] Patent Number: 5,066,281

[45] Date of Patent: Nov. 19, 1991

[54] DISPOSABLE SYRINGE APPARATUS WITH RETRACTABLE NEEDLE, LOCKING DEVICE AND CAP DEVICE

[76] Inventor: Deborah G. C. Stevenson-Michener, 226 E. Flag Swamp Rd., Southbury, Conn. 06488

[21] Appl. No.: 498,957

[22] Filed: Mar. 26, 1990

[51] Int. Cl.[5] .......... A61M 5/50

[52] U.S. Cl. .......... 604/110; 604/195; 604/218

[58] Field of Search .......... 604/110, 194–196, 604/218, 207–211

[56] References Cited

U.S. PATENT DOCUMENTS

| | | | |
|---|---|---|---|
| 3,107,785 | 10/1963 | Roehr | 604/194 X |
| 4,731,068 | 3/1988 | Hesse | 604/110 |
| 4,804,370 | 2/1989 | Haber et al. | 604/195 |
| 4,826,483 | 5/1989 | Molnar, IV | 604/110 |
| 4,832,694 | 5/1989 | Raphael, III et al. | 604/110 |
| 4,836,373 | 6/1989 | Goldman | 206/366 |
| 4,906,231 | 3/1990 | Young | 604/110 |
| 4,908,023 | 3/1990 | Yuen | 604/118 |
| 4,932,939 | 6/1990 | Magre et al. | 604/110 |
| 4,995,874 | 2/1991 | Strickland | 604/195 |

*Primary Examiner*—John D. Yasko
*Assistant Examiner*—Adam J. Cermak

[57] ABSTRACT

A disposable syringe apparatus with retractable body entering conduit which reduces the frequency of accidental needle strikes to health care workers and prevents health-threatening reuse of the syringe by drug abusers. The device includes a cylinder having an open proximal end, a closed distal end, and a body entering conduit projecting through the distal end. A piston assembly is included having a member at its distal end for engaging the aperture at the proximal end of the body entering conduit following expulsion of fluid materials. The piston is then withdrawn proximally through the cylinder relocating the body entering conduit fully within the interior of the cylinder. The body entering conduit and piston are locked in place by a member for a tapering cam on the exterior of the piston and retainers on the interior of the cylinder. The distal end of cylinder is then frictionally engaged in the syringe cap as it awaits on a plane surface thereby rendering the body entering conduit permanently irretrievable and the cylinder aperture safely locked closed.

6 Claims, 4 Drawing Sheets

DISPOSABLE SYRINGE APPARATUS WITH RETRACTABLE NEEDLE, LOCKING DEVICE AND CAP DEVICE

BACKGROUND OF THE INVENTION

1. Field of the Invention

The apparatus of the present embodiment of the invention relates to syringes. More particularly, the apparatus of the present embodiment of the invention relates to syringes having a body entering conduit which is retractable prior to or after injection, having a piston movable reciprocally and axially within a cylinder portion, having a piston locking device and a cap device providing protection for the aperture for the body entering conduit following retraction.

2. Prior Art

Syringes are used for the injection or removal of fluent material for a variety of necessary medical procedures. However, after the injection procedure is completed, problems may arise as a consequence of contamination of the needles. By way of example, the syringe may be used to treat a patient having a communicable disease. Due to improper disposal of these syringes and/or through general use or misuse of them, health care workers themselves have been infected with the diseases they have attempted to treat, such as AIDS, due to accidental needle strikes. Also, by way of example, drug users have been able to obtain previously used and infected syringes. It is known that such syringes have been used in an illicit capacity thereby furthering the spread of contagious diseases.

The following U.S. Pat. No. provide examples of syringes having a needle which may be retracted into the syringe cylinder after use:

U.S. Pat. No. 4,804,370; Feb. 14, 1989
U.S. Pat. No. 4,826,484; May 2, 1989
U.S. Pat. No. 4,826,489; May 2, 1989
U.S. Pat. No. 4,836,373; Jun. 6, 1989

Whatever the precise merits, features and advantages of the above cited references, none of them have the means by which the needle may be retracted within and shielded by the syringe cylinder by means of a hooking device, a piston locking device and cylinder capping device as hereinafter described so as to lessen the number of accidental needle strikes and the possible spread of disease. Moreover, with respect to the capping device, little is available providing free standing, finger protecting syringe cylinder aperture covering following needle retraction.

SUMMARY OF THE INVENTION

Disclosed is a disposable syringe and capping device which overcomes the problems inherent in conventional syringes by providing health care workers a reliable means of injecting fluent materials which is safe not only for the patient but also for those giving the injection. This is accomplished by providing a means to prevent disease transmission from accidental needle strikes while also preventing reuse of the needle by drug users.

The apparatus of the preferred embodiment of the invention solves the problems of the current state of the art in a simple manner. What is provided is a syringe apparatus comprising a syringe cylinder or barrel with an open proximal end and a substantially closed distal end with a means for frictional sealing at the distal end. Also provided is a piston adapted for reciprocal and axial movement through the syringe cylinder having a means for detachable connection to the proximal end of the body entering conduit by a means for a hooking device, a body entering conduit projecting from the distal end of the cylinder with a means for an aperture at the proximal end as a means for detachable connection to the distal end of the piston providing for the retraction of the body entering conduit within the cylinder. Also provided is a means for locking the piston with the attached retracted body entering conduit within the cylinder by reciprocal and axial movement of a tapering spiral ribbed cam on the exterior of the piston and ribbed retainers on the interior of the cylinder, and a syringe cylinder cap with a flat closed base at the proximal end and an open distal end for receiving and frictionally engaging the cylinder following retraction of the body entering conduit.

DESCRIPTION OF THE DRAWINGS

FIG. 2.1. illustrates the operational step of the preferred embodiment moving the piston axially within the cylinder to engage the connection of the conduit to the piston.

FIG. 2.2. illustrates the operational step of the preferred embodiment moving the piston proximally through the cylinder for retracting the body entering conduit within the cylinder.

FIG. 2.3 illustrates the operational step of the preferred embodiment moving the piston axially and reciprocally within the cylinder to engage the piston locking device.

FIG. 2.4 illustrates the operational step of the preferred embodiment moving the entire syringe unit with the body entering conduit in the retracted position so that the distal end can be received and frictionally engaged by the cylinder cap.

FIG. 3.1 is a sectional view of the tapering spiral rib cam shown on line 3.1—3.1 in FIG. 3.

Figure 1:
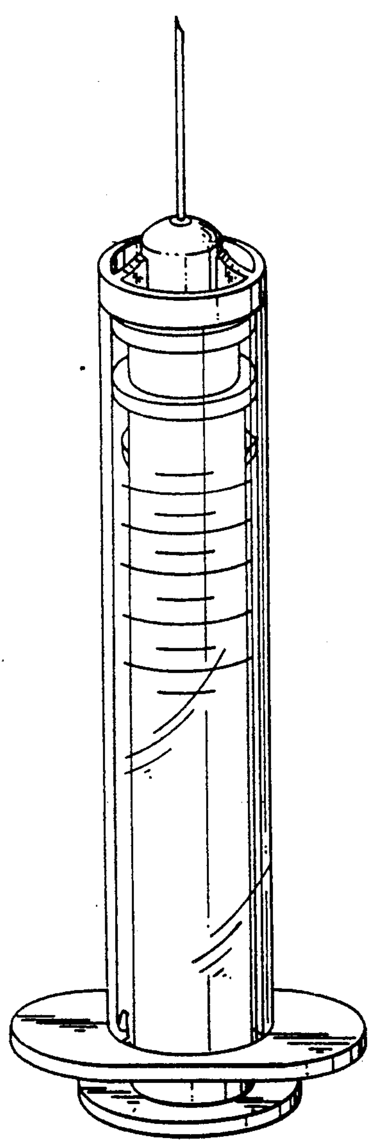
FIG. 1 is a view of a typical 1 cc syringe comprising an example of the preferred embodiment of the invention.

All measurements on drawings provided are approximate and intended only to aid in understanding the drawings. All language in the drawings similarly is only intended for a better understanding and not intended as necessary to the preferred embodiment.

DETAILED DESCRIPTION OF THE PREFERRED EMBODIMENT

The preferred embodiment of the disease control syringe apparatus having a retractable body entering conduit, piston locking device and capping device which forms the present invention is best described while referring to the drawings.

In FIG. 1 there is shown an overall view of one type of syringe, a typical 1 cc, of which could comprise the preferred embodiment of the present invention. There is shown a generally cylindrical barrel or cylinder having an open proximal end and a substantially closed distal end. The cylinder portion would also comprise flange shoulder portions extending outwardly from the surface to provide a gripping means for fingers of the health care workers during use of the apparatus.

Figure 2:
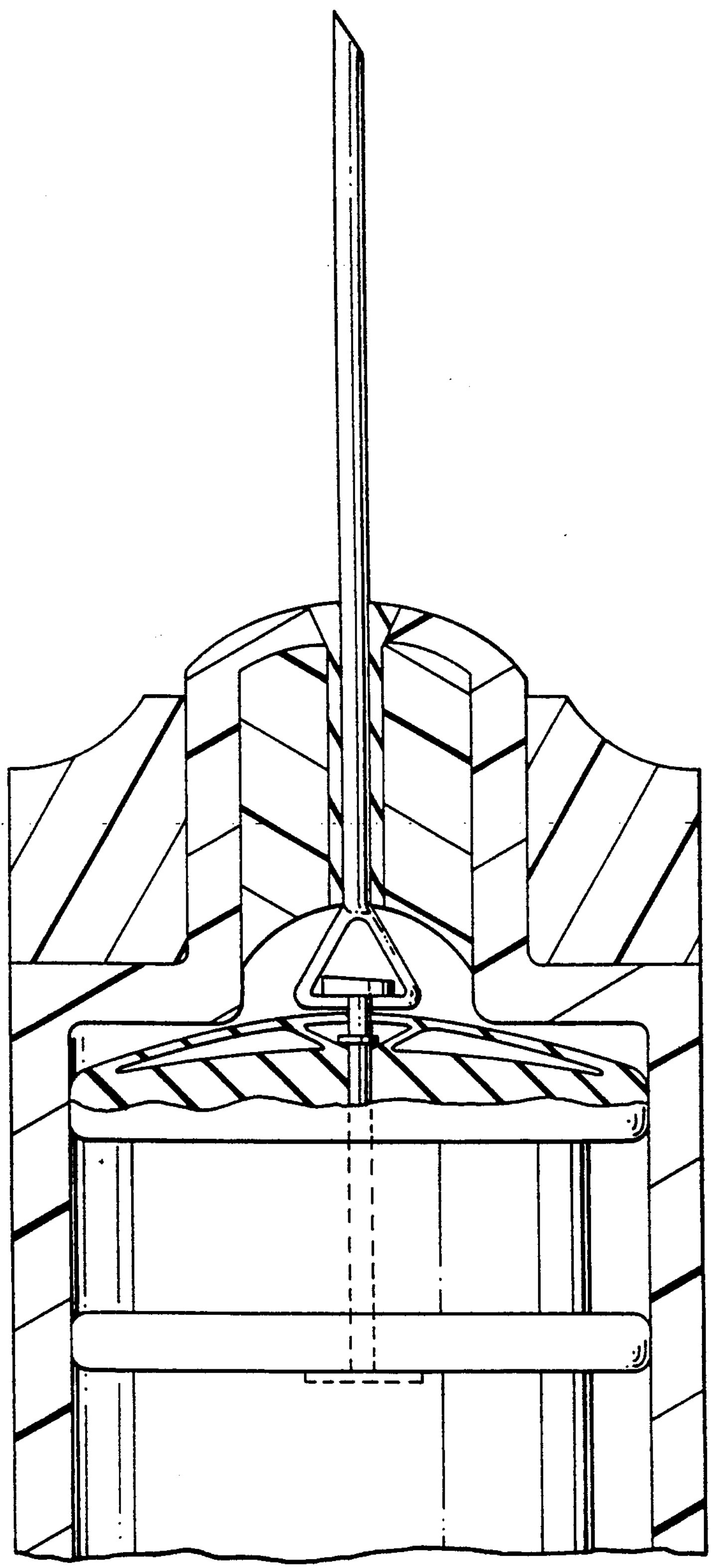
FIG. 2 is an enlarged cross-section showing the preferred embodiment of a body entering conduit projecting from the distal end of the cylinder and the preferred embodiment of the means for the detachable connection of the conduit to the distal end of the piston and its anchoring device.
Figure 2A:
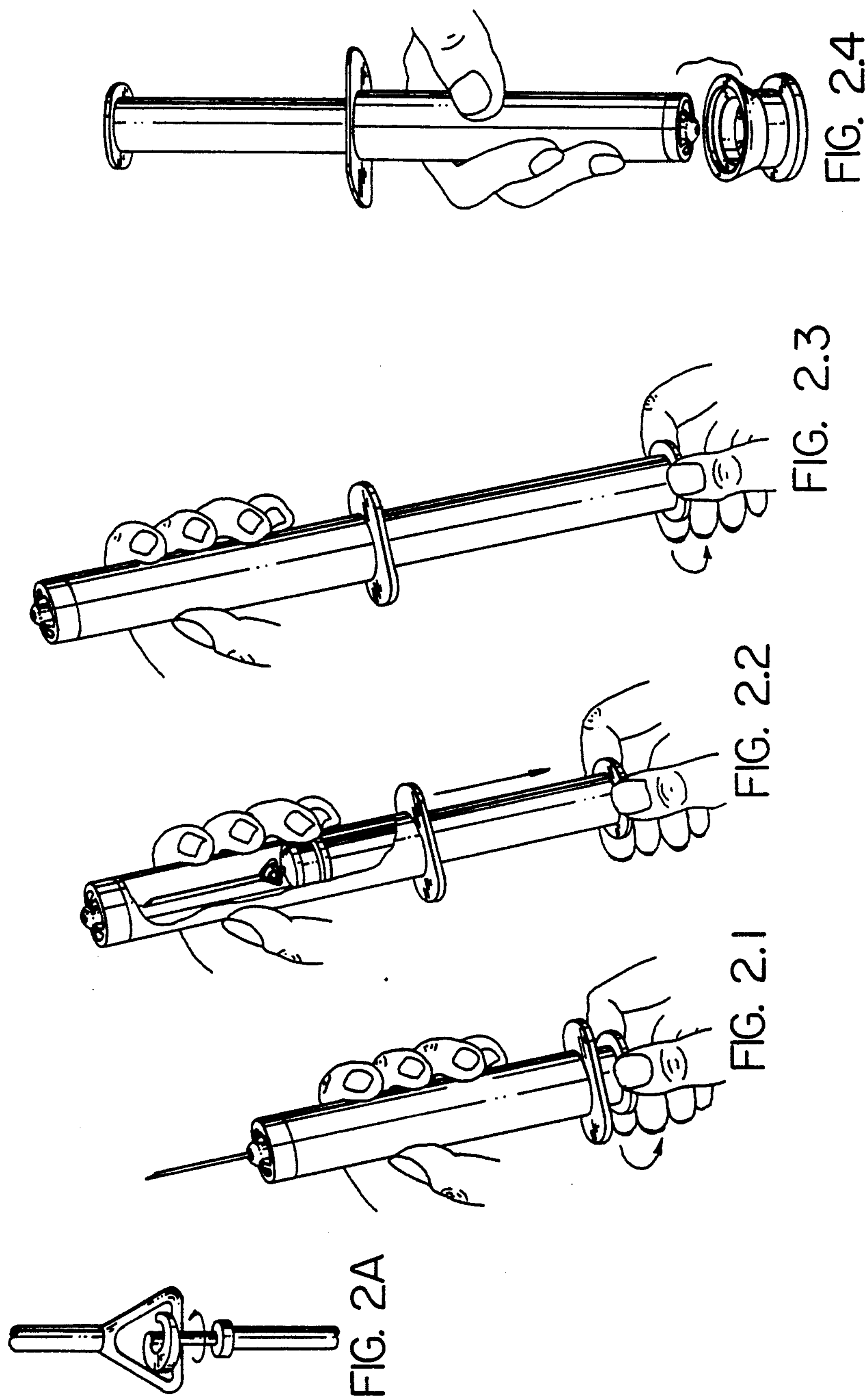
FIG. 2A is a perspective view of the piston and needle releasable connection means.

In FIG. 2 a means for frictional sealing of the distal end is disposed within the distal end of the cylinder. This sealing means is shown as a self sealing rubber sleeve around the needle. A body entering conduit is shown in FIG. 2 which extends through the frictional sealing means for use and is moved proximally through and out of the sealing means after use. The proximal end of the body entering conduit is shown having an aperture for reciprocal connection with the distal end of the piston. Thus, the piston has a crescent shaped hook element secured in its face for releasably engaging the eye portion of the syringe needle as suggested in FIG. 2A. As shown the distal end of the piston has a semi-circular means for releasable connection with the proximal end of the body entering conduit and a means for anchoring at its more distal end within the piston this means being shown as a hook anchored into the plastic plunger shaft, as required.

Figure 3:
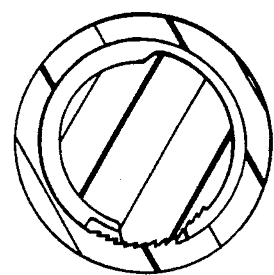
FIG. 3 shows an enlarged cross-sectional detail of the means for the preferred embodiment of the piston locking device.
Figure 3:
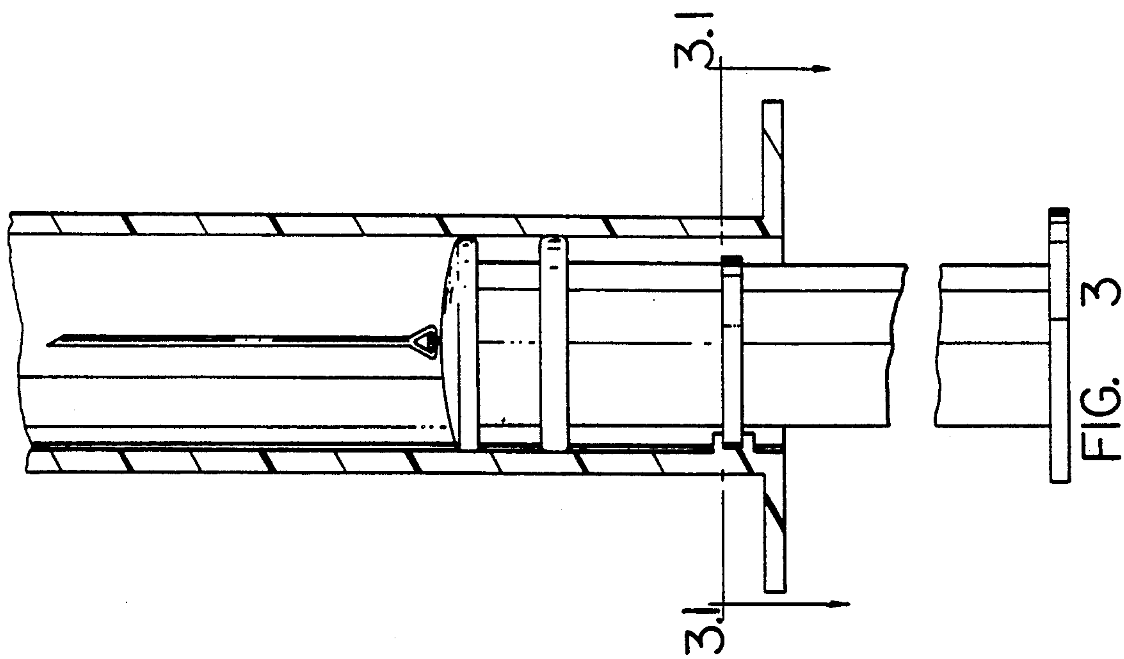

As shown in FIGS. 3 and 3.1 the piston can be locked in place within the cylinder as a result of twisting the piston relative to the cylinder as suggested in FIG. 2.3. Formed around the proximal end of the piston is a tapering spiral cam. Formed around the interior of the cylinder are retainers used as a means for reciprocal connection with the tapering cam. Both the piston cam and the cylinder retainers are shown as formed with a plural ribbing means allowing for only one way, one time use of the syringe apparatus when engaged.

Figure 4B:
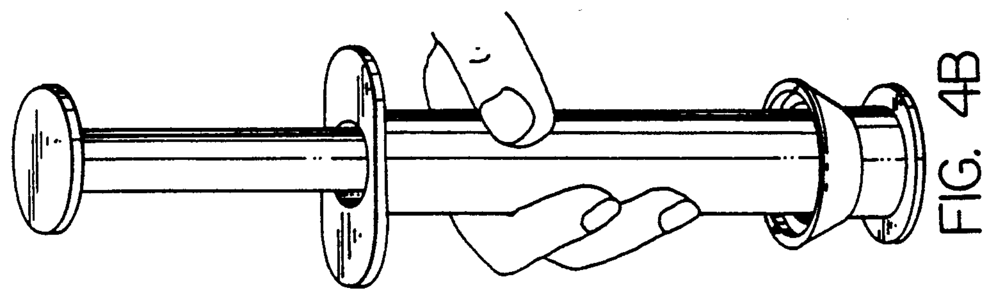
FIG. 4B shows an overall view of the preferred embodiment of the syringe unit with the body entering conduit in the retracted position and the cylinder cap engaged in the locked position on the distal end of the cylinder.
Figure 4A:
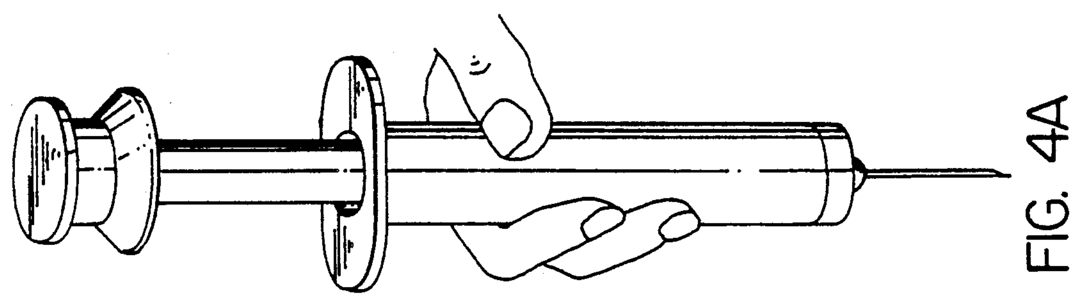
FIG. 4A shows an overall view of the preferred embodiment of the syringe unit with the cylinder cap in place in the stored position.
Figure 4:
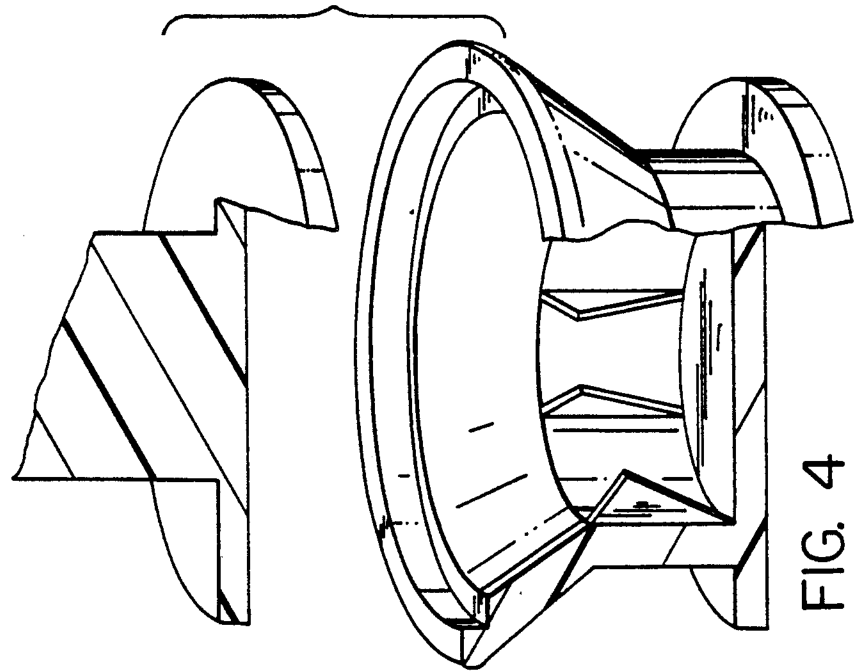
FIG. 4 shows an enlarged cross-section of the preferred embodiment of the cylinder cap as it is positioned for storage on the proximal end of the piston prior to use.

FIG. 4 shows the enlarged detail of the interior of the Preferred embodiment of the syringe cylinder cap. The distal end of the cap is open to receive the syringe cylinder after conduit use and retraction and piston locking. The most distal aspect of the cap is formed to frictionally connect with and snap onto the most proximal end of the piston prior to use of the syringe apparatus. The adjacent circumference of the most distal aspect of the cap is formed to frictionally engage with the distal end of the cylinder after use of the syringe apparatus also utilizing a means for a plurality of locking tabs within the cap. The base at the proximal end of the cap is closed and is formed flat so as to be positioned freely on a plane surface to await receipt of the distal end of the cylinder.

FIG. 4B shows the preferred embodiment of the syringe apparatus prior to use with the syringe cap affixed to the proximal end of the piston on the thumb of the plunger.

FIG. 4B shows the preferred embodiment of the syringe apparatus with the body entering conduit in the retracted position, the piston in the locked position and the syringe cap engaged at the distal end of the cylinder.

FIG. 2.1., FIG. 2.2, FIG. 3 and FIG. 4 illustrate the operational use of the preferred embodiment of the syringe apparatus. FIG. 2.1. shows the rotational movement of the piston within the cylinder to engage the means for connection at the distal end of the piston and the proximal end of the body entering conduit following injection of the fluent material. This is done by twisting the plunger to hook the eye of needle FIG. 2.2 shows the piston and engaged body entering conduit being moved toward the proximal end of the cylinder until the conduit is completely retracted inside the cylinder and the means for sealing the distal end of the cylinder has been activated. FIG. 3 shows the piston being rotationally moved so that the means for the piston tapering cam and the interior cylinder retainers are engaged locking the shaft and the body entering conduit irretrievably within the cylinder. FIG. 4B shows the insertion of the locked cylinder into the distal end of the syringe cap frictionally engaging its locking means and rendering the syringe apparatus safe for handling and disposal.

It will be apparent that while a preferred embodiment of the invention has been shown and described, various modifications and changes may be made without departing from the true spirit and scope of the invention. It is to be understood, then, that the details herein are to be interpreted as illustrative and not in a limiting sense.

What is claimed as invention is:

1. A syringe apparatus which comprises:

a) a substantially cylindrical hollow barrel portion herein described as cylinder having a substantially closed distal end and an open proximal end and having flange shoulder portions extending outwardly form the cylinder surface at the proximal end as a gripping means;

b) a body entering conduit at least partially contained within said hollow cylinder portion and at times partially extruding therefrom;

c) a means for the frictional sealing at the distal end of the cylinder so that the distal end remains closed after retraction of the body entering conduit;

d) a piston assembly movable reciprocally and axially through said cylinder;

e) means for detachably connecting the proximal end of the body entering conduit to said piston assembly distal end so that when said conduit and said assembly are connected said piston moves in unison with said body entering conduit;

f) means for detachably connecting the distal end of the piston assembly to said proximal end of the body entering conduit so that when said conduit and said assembly are connected said conduit moves in unison with said piston;

g) means for anchoring said detachable piston connecting means at said piston assembly distal end;

h) means for locking the piston assembly and the attached body entering conduit within the cylinder following retraction of the body entering conduit within the cylinder by reciprocal and axial movement thereof, said means comprising a tapering spiral ribbed cam on the piston;

i) said means for locking the piston assembly and the detachably connected body entering conduit within the cylinder following retraction of the body entering conduit within the cylinder further comprising ribbed retainers on the interior of the cylinder allowing for only one way, one time use of the syringe apparatus when engaged with said cam.

2. The syringe apparatus as defined in claim 1, further comprising:

a cap for said syringe, said cap comprising:

a) a hollow cylindrical portion having a flared, open distal end and a closed proximal end for mounting said device on a plane surface;

b) means at the distal end of said cap for frictionally connecting with the most proximal end of the syringe piston assembly prior to use of the syringe;

c) means around the circumference of the distal end of the cap for frictionally connecting with the distal end of the syringe;

d) said cap distal end frictionally connecting means comprising a plurality of locking tabs around the interior circumference of the cylindrical cap.

3. The apparatus in claim 1 wherein said body entering conduit comprises a means for an aperture at its proximal end;

a. said means detachably connecting with the distal end of the piston so that the body entering conduit moves in unison with said piston reciprocally through said syringe cylinder toward the proximal end of the cylinder such that the conduit extends completely within the interior of the cylinder.

4. The apparatus in, claim 1 wherein said piston comprises a hooking means and an attached anchoring device for anchoring said hooking means at the distal end of said piston;

a. said hooking means detachably connecting with the proximal end of the body entering conduit so that the conduit moves in unison with said piston reciprocally through said cylinder toward the proximal end of the cylinder such that the conduit extends completely within the interior of the cylinder.

5. A method of retracting a body entering conduit of a syringe following injection and capping said syringe comprising the following steps:

a. providing a syringe cap apparatus having a substantially cylindrical hollow portion with means to attach to and detach from the proximal end of the syringe piston;

b. detaching said cap;

c. placing said cap on a plane surface awaiting receipt of the cylinder;

d. providing a syringe apparatus having a substantially cylindrical hollow barrel portion open at the proximal end and substantially closed at the distal end;

e. providing a body entering conduit protruding through a sealing device at the distal end of the cylinder and movable to a retracted position within the cylinder:

f. providing a piston portion insertable into the hollow of said cylinder portion and movable within said cylinder;

g. providing a means for engaging the body entering conduit to the distal end of the piston;

h. inserting said piston portion into said cylinder;

i. preparing said body entering conduit and piston for injecting fluid to be administered;

j. inserting said body entering conduit into the fluid to be administered;

k. retracting said piston thus drawing fluid into the area between said body entering conduit and said piston within the cylinder;

l. inserting the conduit into patient;

m. plunging piston into a position adjacent to body entering conduit thus forcing said fluid into said patient;

n. withdrawing body entering conduit from patient;

o. engaging devices connecting proximal end of body entering conduit to distal end of piston;

p. retracting said conduit until entire body entering conduit is within interior syringe cylinder;

q. engaging means comprising a tapering spiral ribbed cam on said piston and ribbed retainers on interior cylinder wall as a means for locking the body entering conduit and piston within the cylinder;

r. engaging distal end of cylinder to syringe cap by frictional pressure.

6. The method in claim 5 further comprising the step of disposing of said apparatus following the retraction of said body entering conduit into said cylinder and capping of said cylinder.

* * * * *